(12) United States Patent
Trieu

(10) Patent No.: US 7,520,888 B2
(45) Date of Patent: Apr. 21, 2009

(54) TREATMENT OF THE VERTEBRAL COLUMN

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 382 days.

(21) Appl. No.: 11/353,520

(22) Filed: Feb. 14, 2006

(65) Prior Publication Data

US 2007/0213824 A1  Sep. 13, 2007

(51) Int. Cl.
  *A61B 17/70* (2006.01)
  *A61F 2/44* (2006.01)
(52) U.S. Cl. .................. 606/279; 606/248; 623/17.12
(58) Field of Classification Search ... 623/17.11–17.16; 606/61, 248, 279
  See application file for complete search history.

(56) References Cited

U.S. PATENT DOCUMENTS

| | | | |
|---|---|---|---|
| 4,969,888 A | 11/1990 | Scholten et al. |
| 5,015,247 A | 5/1991 | Michelson |
| 5,015,255 A | 5/1991 | Kuslich |
| 5,062,845 A | 11/1991 | Kuslich et al. |
| 5,108,404 A | 4/1992 | Scholten et al. |
| 5,171,279 A | 12/1992 | Mathews |
| 5,357,983 A | 10/1994 | Mathews |
| 5,375,823 A | 12/1994 | Navas |
| 5,445,639 A | 8/1995 | Kuslich et al. |
| 5,480,401 A | 1/1996 | Navas |
| 5,496,322 A | 3/1996 | Mathews |
| 5,540,688 A | 7/1996 | Navas |
| 5,569,248 A | 10/1996 | Mathews |
| 5,645,084 A | 7/1997 | McKay |
| 5,674,295 A | 10/1997 | Ray et al. |
| 5,674,296 A | 10/1997 | Bryan et al. |
| 5,702,453 A | 12/1997 | Rabbe et al. |
| 5,728,097 A | 3/1998 | Mathews |
| 5,776,197 A | 7/1998 | Rabbe et al. |
| 5,776,198 A | 7/1998 | Rabbe et al. |
| 5,792,044 A | 8/1998 | Foley et al. |
| 5,836,948 A | 11/1998 | Zucherman et al. |
| 5,860,977 A | 1/1999 | Zucherman et al. |
| 5,865,846 A | 2/1999 | Bryan et al. |
| 5,876,404 A | 3/1999 | Zucherman et al. |
| 5,888,220 A | 3/1999 | Felt et al. |
| 5,902,231 A | 5/1999 | Foley et al. |

(Continued)

FOREIGN PATENT DOCUMENTS

FR  2870718 A1 * 12/2005

(Continued)

OTHER PUBLICATIONS

Susan M. Rapp; *Cells in middle of disc that are low in glucose at risk of dying*; Jan. 3, 2006.

*Primary Examiner*—Eduardo C Robert
*Assistant Examiner*—Ellen Rust
(74) *Attorney, Agent, or Firm*—Haynes and Boone, LLP

(57) ABSTRACT

A method is provided for treating a spinal condition. The method includes introducing a biological treatment into an area of a vertebral column, and mechanically unloading the treated area by applying a load-bearing device to the anterior region, the anterior column region, the posterior region, or the spinous process region of the vertebral column.

24 Claims, 7 Drawing Sheets

U.S. PATENT DOCUMENTS

| | | |
|---|---|---|
| 5,928,239 A | 7/1999 | Mirza |
| 5,954,635 A | 9/1999 | Foley et al. |
| 5,980,504 A | 11/1999 | Sharkey et al. |
| 5,984,967 A | 11/1999 | Zdeblick et al. |
| 6,007,487 A | 12/1999 | Foley et al. |
| 6,007,570 A | 12/1999 | Sharkey et al. |
| 6,033,406 A | 3/2000 | Mathews |
| 6,033,438 A | 3/2000 | Bianchi et al. |
| 6,095,149 A | 8/2000 | Sharkey et al. |
| 6,113,637 A | 9/2000 | Gill et al. |
| 6,122,549 A | 9/2000 | Sharkey et al. |
| 6,126,682 A | 10/2000 | Sharkey et al. |
| 6,152,871 A | 11/2000 | Foley et al. |
| 6,156,067 A | 12/2000 | Bryan et al. |
| 6,162,170 A | 12/2000 | Foley et al. |
| 6,162,252 A | 12/2000 | Kuras et al. |
| 6,176,823 B1 | 1/2001 | Foley et al. |
| 6,206,822 B1 | 3/2001 | Foley et al. |
| 6,217,509 B1 | 4/2001 | Foley et al. |
| 6,224,604 B1 | 5/2001 | Suddaby |
| 6,241,734 B1 | 6/2001 | Scribner et al. |
| 6,248,110 B1 | 6/2001 | Reiley et al. |
| 6,248,131 B1 | 6/2001 | Felt et al. |
| 6,344,057 B1 | 2/2002 | Rabbe et al. |
| 6,371,988 B1 | 4/2002 | Pafford et al. |
| 6,419,702 B1 * | 7/2002 | Ferree ............... 623/17.11 |
| 6,425,859 B1 | 7/2002 | Foley et al. |
| 6,440,138 B1 | 8/2002 | Reiley et al. |
| 6,478,822 B1 | 11/2002 | Leroux et al. |
| 6,517,568 B1 | 2/2003 | Sharkey et al. |
| 6,520,907 B1 | 2/2003 | Foley et al. |
| 6,540,785 B1 | 4/2003 | Gill et al. |
| 6,558,386 B1 | 5/2003 | Cragg |
| 6,558,390 B2 | 5/2003 | Cragg |
| 6,575,899 B1 | 6/2003 | Foley et al. |
| 6,575,919 B1 | 6/2003 | Reiley et al. |
| 6,582,439 B1 | 6/2003 | Sproul |
| 6,582,446 B1 | 6/2003 | Marchosky |
| 6,582,467 B1 | 6/2003 | Teitelbaum et al. |
| 6,592,625 B2 | 7/2003 | Cauthen |
| 6,592,664 B1 | 7/2003 | Frey et al. |
| 6,599,291 B1 | 7/2003 | Foley et al. |
| 6,613,018 B2 | 9/2003 | Bagga et al. |
| 6,613,054 B2 | 9/2003 | Scribner et al. |
| 6,613,091 B1 | 9/2003 | Zdeblick et al. |
| 6,620,162 B2 | 9/2003 | Kuslich et al. |
| 6,620,196 B1 | 9/2003 | Trieu |
| 6,626,944 B1 * | 9/2003 | Taylor ............... 623/17.16 |
| 6,641,587 B2 | 11/2003 | Scribner et al. |
| 6,648,916 B1 | 11/2003 | McKay |
| 6,666,891 B2 | 12/2003 | Boehm, Jr. et al. |
| 6,669,732 B2 | 12/2003 | Serhan et al. |
| 6,676,665 B2 | 1/2004 | Foley et al. |
| 6,679,886 B2 | 1/2004 | Weikel et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,723,335 B1 * | 4/2004 | Moehlenbruck et al. .... 424/425 |
| 6,726,691 B2 | 4/2004 | Osorio et al. |
| 6,730,095 B2 | 5/2004 | Olson, Jr. et al. |
| 6,740,118 B2 | 5/2004 | Eisermann et al. |
| 6,746,451 B2 | 6/2004 | Middleton et al. |
| 6,761,720 B1 | 7/2004 | Senegas |
| 6,770,079 B2 | 8/2004 | Bhatnagar et al. |
| 6,780,191 B2 | 8/2004 | Sproul |
| 6,780,192 B2 | 8/2004 | McKay et al. |
| 6,786,930 B2 * | 9/2004 | Biscup ............... 623/16.11 |
| 6,805,715 B2 | 10/2004 | Reuter et al. |
| 6,949,123 B2 | 9/2005 | Reiley |
| 6,969,404 B2 * | 11/2005 | Ferree ............... 623/17.11 |
| 7,445,637 B2 * | 11/2008 | Taylor ............... 623/17.16 |
| 2001/0020188 A1 | 9/2001 | Sander |
| 2002/0016583 A1 | 2/2002 | Cragg |
| 2002/0016616 A1 | 2/2002 | McGraw et al. |
| 2002/0029082 A1 | 3/2002 | Muhanna |
| 2002/0045942 A1 | 4/2002 | Ham |
| 2002/0045944 A1 | 4/2002 | Muhanna et al. |
| 2002/0076400 A1 | 6/2002 | Katz et al. |
| 2002/0099384 A1 | 7/2002 | Scribner et al. |
| 2002/0099385 A1 | 7/2002 | Ralph et al. |
| 2002/0115742 A1 | 8/2002 | Trieu et al. |
| 2002/0120336 A1 | 8/2002 | Santilli |
| 2002/0128718 A1 | 9/2002 | Ferree |
| 2002/0132334 A1 | 9/2002 | Jessell et al. |
| 2002/0150971 A1 | 10/2002 | Johansen et al. |
| 2002/0151893 A1 | 10/2002 | Santilli |
| 2002/0156483 A1 | 10/2002 | Voellmicke et al. |
| 2002/0165542 A1 | 11/2002 | Ferree |
| 2002/0168663 A1 | 11/2002 | Phan et al. |
| 2002/0172980 A1 | 11/2002 | Phan et al. |
| 2002/0173796 A1 | 11/2002 | Cragg |
| 2003/0003464 A1 | 1/2003 | Phan et al. |
| 2003/0004574 A1 | 1/2003 | Ferree |
| 2003/0009227 A1 | 1/2003 | Lambrecht et al. |
| 2003/0044421 A1 | 3/2003 | Emini et al. |
| 2003/0045937 A1 | 3/2003 | Ginn |
| 2003/0054331 A1 | 3/2003 | Fraser et al. |
| 2003/0054376 A1 | 3/2003 | Mullis et al. |
| 2003/0055427 A1 | 3/2003 | Graf |
| 2003/0069639 A1 * | 4/2003 | Sander et al. ............ 623/17.11 |
| 2003/0082152 A1 | 5/2003 | Hedrick et al. |
| 2003/0082568 A1 | 5/2003 | Phan et al. |
| 2003/0086936 A1 | 5/2003 | Souza |
| 2003/0118545 A1 | 6/2003 | Shi et al. |
| 2003/0129665 A1 | 7/2003 | Selvan et al. |
| 2003/0130664 A1 | 7/2003 | Boucher et al. |
| 2003/0153849 A1 | 8/2003 | Huckle et al. |
| 2003/0161816 A1 | 8/2003 | Fraser et al. |
| 2003/0162707 A1 | 8/2003 | Fraser et al. |
| 2003/0171814 A1 | 9/2003 | Muhanna et al. |
| 2003/0180266 A1 | 9/2003 | McKay et al. |
| 2003/0181964 A1 | 9/2003 | Sharkey et al. |
| 2003/0191474 A1 | 10/2003 | Cragg et al. |
| 2003/0195518 A1 | 10/2003 | Cragg |
| 2003/0195630 A1 | 10/2003 | Ferree |
| 2003/0199871 A1 | 10/2003 | Foley et al. |
| 2003/0216736 A1 | 11/2003 | Robinson et al. |
| 2003/0219423 A1 | 11/2003 | Gazit et al. |
| 2003/0219713 A1 | 11/2003 | Valencia et al. |
| 2003/0219843 A1 | 11/2003 | Welsch et al. |
| 2003/0220283 A1 | 11/2003 | Glorioso et al. |
| 2003/0228292 A1 | 12/2003 | Gazit et al. |
| 2003/0229353 A1 | 12/2003 | Cragg |
| 2003/0233096 A1 | 12/2003 | Osorio et al. |
| 2004/0024081 A1 | 2/2004 | Trieu et al. |
| 2004/0024410 A1 | 2/2004 | Olson, Jr. et al. |
| 2004/0030392 A1 | 2/2004 | Lambrecht et al. |
| 2004/0033221 A1 | 2/2004 | Masuda et al. |
| 2004/0052829 A1 | 3/2004 | Shimp |
| 2004/0054414 A1 | 3/2004 | Trieu et al. |
| 2004/0064058 A1 | 4/2004 | McKay |
| 2004/0068267 A1 | 4/2004 | Harvie et al. |
| 2004/0083001 A1 | 4/2004 | Kandel |
| 2004/0087947 A1 | 5/2004 | Lim et al. |
| 2004/0091540 A1 | 5/2004 | Desrosiers et al. |
| 2004/0092946 A1 | 5/2004 | Bagga et al. |
| 2004/0097867 A1 | 5/2004 | Fraser et al. |
| 2004/0097928 A1 | 5/2004 | Zdeblick et al. |
| 2004/0097930 A1 | 5/2004 | Justis et al. |
| 2004/0097980 A1 | 5/2004 | Ferree |
| 2004/0101957 A1 | 5/2004 | Emini et al. |
| 2004/0102774 A1 | 5/2004 | Trieu |
| 2004/0106196 A1 | 6/2004 | Fraser et al. |
| 2004/0116927 A1 | 6/2004 | Graf |

| | | |
|---|---|---|
| 2004/0133280 A1 | 7/2004 | Trieu |
| 2004/0153064 A1 | 8/2004 | Foley et al. |
| 2004/0158248 A1 | 8/2004 | Ginn |
| 2004/0171146 A1 | 9/2004 | Katz et al. |
| 2004/0172132 A1 | 9/2004 | Ginn |
| 2004/0193274 A1 | 9/2004 | Trieu |
| 2004/0228853 A1 | 11/2004 | Serhan et al. |
| 2004/0228901 A1 | 11/2004 | Trieu et al. |
| 2004/0253219 A1 | 12/2004 | Hedman |
| 2005/0008626 A1 | 1/2005 | Fraser et al. |
| 2005/0015150 A1 | 1/2005 | Lee |
| 2005/0020945 A1 | 1/2005 | Tosaya et al. |
| 2005/0025755 A1 | 2/2005 | Hedrick et al. |
| 2005/0031666 A1 | 2/2005 | Trieu |
| 2005/0043801 A1 | 2/2005 | Trieu et al. |
| 2005/0048033 A1 | 3/2005 | Fraser et al. |
| 2005/0048034 A1 | 3/2005 | Fraser et al. |
| 2005/0048035 A1 | 3/2005 | Fraser et al. |
| 2005/0048036 A1 | 3/2005 | Hedrick et al. |
| 2005/0048644 A1 | 3/2005 | Hedrick et al. |
| 2005/0055030 A1 | 3/2005 | Falahee |
| 2005/0055094 A1 | 3/2005 | Kuslich |
| 2005/0058632 A1 | 3/2005 | Hedrick et al. |
| 2005/0113923 A1 | 5/2005 | Acker et al. |
| 2005/0118228 A1 | 6/2005 | Trieu |
| 2005/0131405 A1 | 6/2005 | Molz, IV et al. |
| 2005/0136042 A1 | 6/2005 | Betz et al. |
| 2005/0153441 A1 | 7/2005 | Hedrick et al. |
| 2005/0153442 A1 | 7/2005 | Katz et al. |
| 2005/0153849 A1 | 7/2005 | Mishra et al. |
| 2005/0154460 A1 | 7/2005 | Yundt |
| 2005/0154461 A1 | 7/2005 | Humphreys et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0159817 A1 | 7/2005 | Ferree |
| 2005/0164969 A1 | 7/2005 | Blander et al. |
| 2005/0171540 A1 | 8/2005 | Lim et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0182417 A1 | 8/2005 | Pagano |
| 2005/0186628 A1 | 8/2005 | Jessell et al. |
| 2005/0186673 A1 | 8/2005 | Geistlich et al. |
| 2005/0196387 A1 | 9/2005 | Seyedin et al. |
| 2005/0245929 A1 * | 11/2005 | Winslow et al. ............... 606/61 |
| 2005/0260159 A1 | 11/2005 | Hasty et al. |
| 2005/0260174 A1 | 11/2005 | Fraser et al. |
| 2005/0260175 A1 | 11/2005 | Hedrick et al. |
| 2005/0267577 A1 | 12/2005 | Trieu |
| 2005/0273169 A1 | 12/2005 | Purcell |
| 2005/0282275 A1 | 12/2005 | Katz et al. |
| 2006/0247623 A1 * | 11/2006 | Anderson et al. ............ 606/61 |
| 2008/0039943 A1 * | 2/2008 | Le Couedic .............. 623/17.16 |

FOREIGN PATENT DOCUMENTS

| | | |
|---|---|---|
| WO | WO 97/26847 | 7/1997 |
| WO | WO 00/48521 | 8/2000 |
| WO | WO 00/67650 | 11/2000 |
| WO | WO 03/105673 | 12/2003 |
| WO | WO 2005/112835 | 12/2005 |
| WO | WO 2005118015 A1 * | 12/2005 |

* cited by examiner

TREATMENT OF THE VERTEBRAL COLUMN

BACKGROUND

The present application relates generally to treatment of the vertebral column, for example, repairing or regenerating an area of the vertebral column, or reducing or preventing degeneration of an area of the vertebral column.

Disease, degradation, and trauma of the spine can lead to various conditions that require treatment to maintain, stabilize, or reconstruct the vertebral column. For example, degeneration of the facet joints and/or the intervertebral discs due to aging and/or trauma can lead to pain, neurological deficit and/or loss of motions that require treatment to maintain, stabilize, reconstruct and/or regenerate the degenerated levels. Repair/regeneration of such levels via a biological approach is technically challenging at least in part because of the high loading environment present in such levels. Reducing or preventing degeneration of an area of the vertebral column can be similarly challenging.

SUMMARY

The present application relates generally to treatment of the vertebral column, for example, repairing or regenerating an area of the vertebral column, or reducing or preventing degeneration of an area of the vertebral column.

In one embodiment, a method of treating a vertebral column includes introducing a biological treatment into an area of a vertebral column, and at least partially mechanically unloading the treated area. In one aspect, the treated area is mechanically unloaded by applying a load-bearing device to at least one region of the vertebral column. In certain aspects, the load-bearing device is applied to an anterior region, an anterior column region, a posterior region, or a spinous process region of the vertebral column. In one aspect, the treated area comprises a disc space, a vertebral body or an endplate. The treated area is unloaded by applying a load-bearing device to a spinous process region of the vertebral column adjacent to the treated area.

In another embodiment, a method for treating a motion segment of a vertebral column includes accessing a portion of the patient's spinal column, implanting a load-bearing device into the motion segment, and injecting a biological treatment into the motion segment. The load-bearing device at least partially mechanically unloads the motion segment. In one such embodiment, the motion segment of the vertebral column is intact.

Additional embodiments are provided in the following description and the attached drawings.

DETAILED DESCRIPTION

Figure 1:
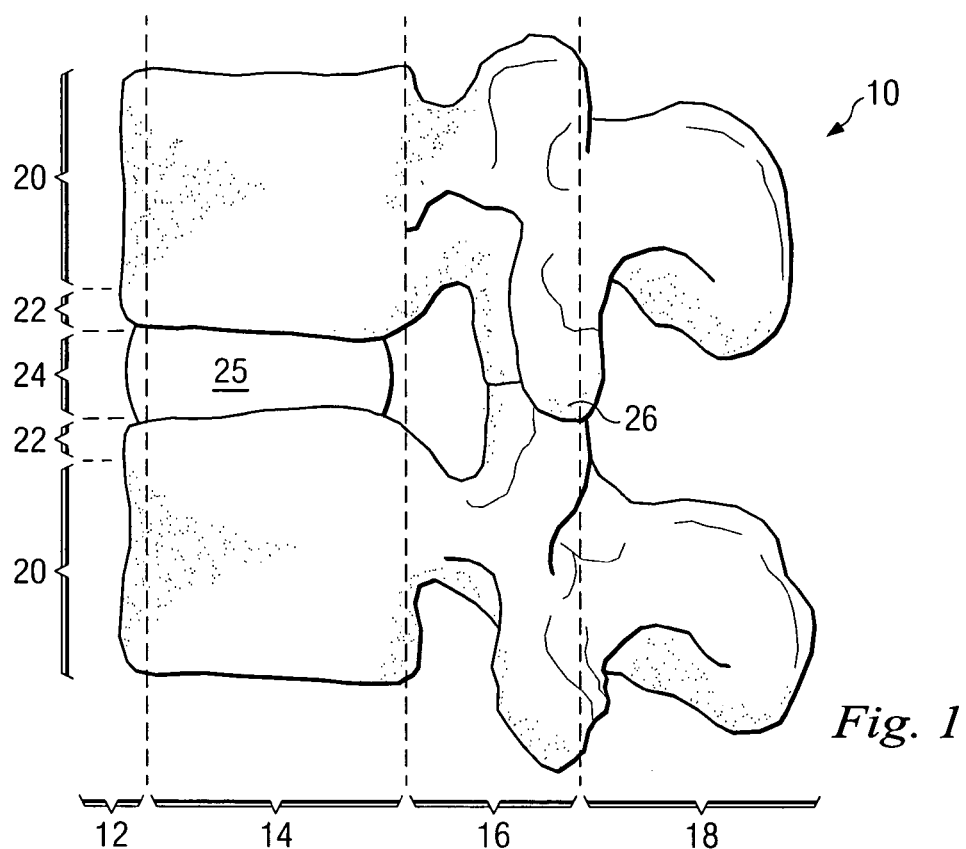
FIG. 1 is a sagittal view of a motion segment of a vertebral column.

The present disclosure relates generally to treatment of the vertebral column, for example, repairing or regenerating an area of the vertebral column, or reducing or preventing degeneration of an area of the vertebral column.

Certain embodiments describe methods for treating motion segments of the spinal column and components thereof. Such embodiments include but are not limited to treating facet joints, intervertebral discs, vertebral bodies and endplates using a biological approach in combination with a mechanical unloading device that is at least partially load-bearing with respect to the treated area such that it at least partially unloads the treated area.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
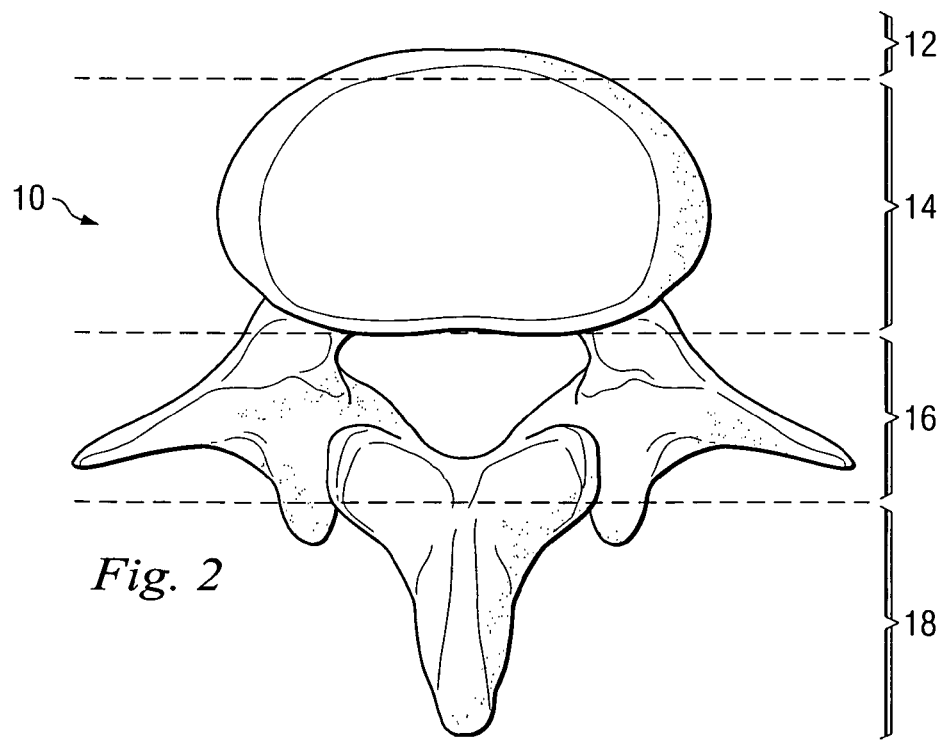
FIG. 2 is a superior view of a vertebral body depicted in FIG. 1.

Referring now to FIGS. 1 and 2, the reference numeral 10 refers to a motion segment of a vertebral column. Motion segment 10 comprises an intervertebral disc 25 and a facet joint 26. Motion segment 10 may be considered as having several regions extending from anterior to posterior. These regions include an anterior region 12, an anterior column region 14, a posterior region 16, and a spinous process region 18. The anterior column region 14 may be further considered to have several regions extending longitudinally along the column. These regions include a vertebral body region 20, an endplate region 22, and a disc space region 24. Disc space region 24 includes the nucleus and annulus forming intervertebral disc 25.

Any of the regions illustrated in FIGS. 1 and 2 may benefit from a biological treatment as described herein. In certain embodiments, the biological treatment is non-load bearing. In certain aspects, a non-load bearing biological treatment comprises a composition that is applied without an associated support or structure. Treatment/treating of the vertebral column includes repair and/or regeneration of a degenerated area of the vertebral column, and/or reduction or prevention of degeneration of an area of the vertebral column. Methods for treating the vertebral column with a biological treatment and a device that is at least partially load-bearing with respect to the treated area such that the device at least partially mechanically unloads the treated area are described herein.

As used herein, a "biological treatment" includes but is not limited to a "biologically active component", with or without a "biological additive".

A "biologically active component" includes but is not limited to anti-cytokines; cytokines; anti-interleukin-1 components (anti-IL-1); anti-TNF alpha; "growth factors"; LIM mineralization proteins; "stem cell material", autogenic chondrocytes; allogenic chondrocytes, such as those described in U.S. Patent Application Publication No. 2005/0196387, the entire disclosure of which is incorporated herein by reference; autogenic chondrocytes with retroviral viral vector or plasmid viral vector; allogenic chondrocytes with retroviral viral vector or plasmid viral vector; and fibroblasts.

The acronym "LIM" is derived from the three genes in which the LIM domain was first described. The LIM domain is a cysteine-rich motif defined by 50-60 amino acids with the consensus sequence $CX_2CX_{16-23}HX_2CX_2CX_2CX_{16-21}CX_2$ (C/H/D), which contains two closely associated zinc-binding modules. LIM mineralization proteins include but are not limited to those described in U.S. Patent Application Publication No. 2003/0180266 A1, the disclosure of which is incorporated herein by reference. "Growth factors" include but are not limited to transforming growth factor (TGF)-beta 1, TGF-beta 2, TGF-beta 3, bone morphogenetic protein (BMP)-2, BMP-3, BMP-4, BMP-6, BMP-7, BMP-9, fibroblast growth factor (FGF), platelet derived growth factor (PDGF), insulin-like growth factor (ILGF); human endothelial cell growth factor (ECGF); epidermal growth factor (EGF); nerve growth factor (NGF); and vascular endothelial growth factor (VEGF). "Anti-IL-1" components include but are not limited to those described in U.S. Patent Application Publication Nos. 2003/0220283 and 2005/0260159, the entire disclosures of which are incorporated herein by reference. "Stem cell material" includes but is not limited to dedifferentiated stem cells, undifferentiated stem cells, and mesenchymal stem cells. "Stem cell material" also includes but is not limited to stem cells extracted from marrow, which may include lipo-derived stem cell material and adipose-derived stem cell material, such as described in U.S. Publication Nos. 2004/0193274 and 2005/0118228, each of which is incorporated herein by reference. "Stem cell material" also includes but is not limited to stem cells derived from adipose tissue as described in U.S. Patent Application Publication Nos. 2003/0161816, 2004/0097867 and 2004/0106196, each of which is incorporated herein by reference.

A "biologically active component" also includes but is not limited to cartilage derived morphogenetic protein (CDMP); cartilage inducing factor (CIP); proteoglycans; hormones; and matrix metalloproteinases (MMP) inhibitors, which act to inhibit the activity of MMPs, to prevent the MMPs from degrading the extracellular matrix (ECM) produced by cells within the nucleus pulposus of the disc. Exemplary MMP inhibitors include but are not limited to tissue inhibitors, such as TIMP-1 and TIMP-2. Certain MMP inhibitors are also described in U.S. Patent Application Publication No. 2004/0228853, the entire disclosure of which is incorporated herein by reference.

A "biologically active component" also includes but is not limited to allogenic or xenogenic disc annulus material, such as described in U.S. Patent Application Publication No. 2005/0043801, the entire disclosure of which is incorporated herein by reference; biologic tissues, such as those described in U.S. Patent Application Publication No. 2003/0004574, the entire disclosure of which is incorporated herein by reference; an activated tissue graft, such as described in U.S. Patent Application Publication No. 2005/0136042, the entire disclosure of which is incorporated herein by reference; an engineered cell comprising a nucleic acid for encoding a protein or variant thereof, such as a BMP, a LIM mineralization protein, or an SMAD protein as described in U.S. Patent Application Publication Nos. 2003/0219423 and 2003/0228292, the entire disclosures of which are incorporated herein by reference; and a recombinant human bone morphogenetic protein, such as described in U.S. Patent Application Publication No. 2004/0024081, the entire disclosure of which is incorporated herein by reference.

As used herein, a "biological additive" includes but is not limited to "biomaterial carriers", "therapeutic agents", "liquids" and "lubricants."

"Biomaterial carriers" include but are not limited to collagen, gelatin, hyaluronic acid, fibrin, albumin, keratin, silk, elastin, glycosaminoglycans (GAGs), polyethylene glycol (PEG), polyethylene oxide (PEO), polyvinyl alcohol (PVA) hydrogel, polyvinyl pyrrolidone (PVP), co-polymers of PVA and PVP, other polysaccharides, platelet gel, peptides, carboxymethyl cellulose, and other modified starches and celluloses. Collagen includes but is not limited to collagen-based material, which may be autogenic, allogenic, xenogenic or of human-recombinant origin, such as the collagen-based material described in U.S. Patent Application Publication Nos. 2004/0054414 and 2004/0228901, the entire disclosures of which are incorporated herein by reference.

"Therapeutic agents" include but are not limited to nutrients, analgesics, antibiotics, anti-inflammatories, steroids, antiviricides, vitamins, amino acids and peptides. Nutrients include but are not limited to substances that promote disc cell survival, such as glucose and pH buffers, wherein the pH buffer provides a basic environment in the disc space, which preferably will be a pH of about 7.4. Analgesics include but are not limited to hydrophilic opoids, such as codeine, pro-drugs, morphine, hydromorphone, propoxyphene, hydrocodone, oxycodone, meperidine and methadone, and lipophilic opoids, such as fentanyl. Antibiotics include but are not limited to erythromycin, bacitracin, neomycin, penicillin, polymyxin B, tetracyclines, viomycin, chloromycetin and streptomycins, cefazolin, ampicillin, azactam, tobramycin, clindamycin and gentamycin.

"Liquids" include but are not limited to water, saline and radio-contrast media. Radio-contrast media includes but is not limited to barium sulfate, or a radio contrast dye, such as sodium diatrizoate (HYPAQUE™).

"Lubricants" include but are not limited to hyaluronic acid, a salt of hyaluronic acid, sodium hyaluronate, glucosaminoglycan, dermatan sulfate, heparin sulfate, chondroitin sulfate, keratin sulfate, synovial fluid, a component of synovial fluid, vitronectin and rooster comb hyaluronate.

A biological treatment may be introduced to an area of a vertebral column, such as a motion segment, by any method and in any form appropriate for such introduction. For example, the biological treatment can be injected, deposited, or applied, as a solution, a suspension, emulsion, paste, a particulate material, a fibrous material, a plug, a solid, porous, woven or non-woven material, or in a dehydrated or rehydrated state. Suitable forms for a biological treatment and suitable methods for injecting a biological treatment include those described in U.S. Patent Application Publication Nos. 2005/0267577, 2005/0031666, 2004/0054414, and 2004/0228901, each of which is incorporated herein by reference.

Figure 3:
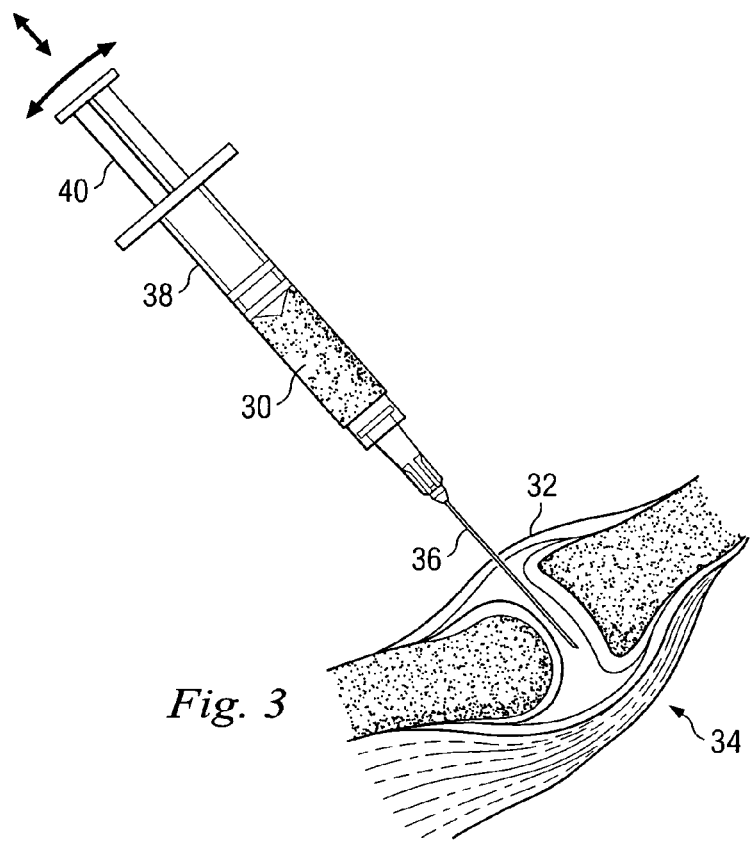
FIGS. 3-4 illustrate methods for applying a biological treatment to a facet joint in a vertebral column.

For example, referring now to FIG. 3, a biological treatment 30 may be injected into the joint capsule 32 of a facet joint 34 through a hypodermic needle 36 attached to a syringe 38. The syringe 38 is inserted into the joint capsule 32, and the syringe plunger 40 is depressed, thereby releasing the biological treatment into the joint capsule of the facet joint. As illustrated by the arrows in FIG. 3, the needle/syringe assembly may be moved around within the joint capsule, sweeping from side to side and back and forth, to ensure uniform distribution of the biological treatment within the facet joint. It is preferred, however, that the tip of the needle be maintained near the center of the joint capsule to ensure deposition of the material within the desired area, and to minimize potential leakage.

Figure 4:
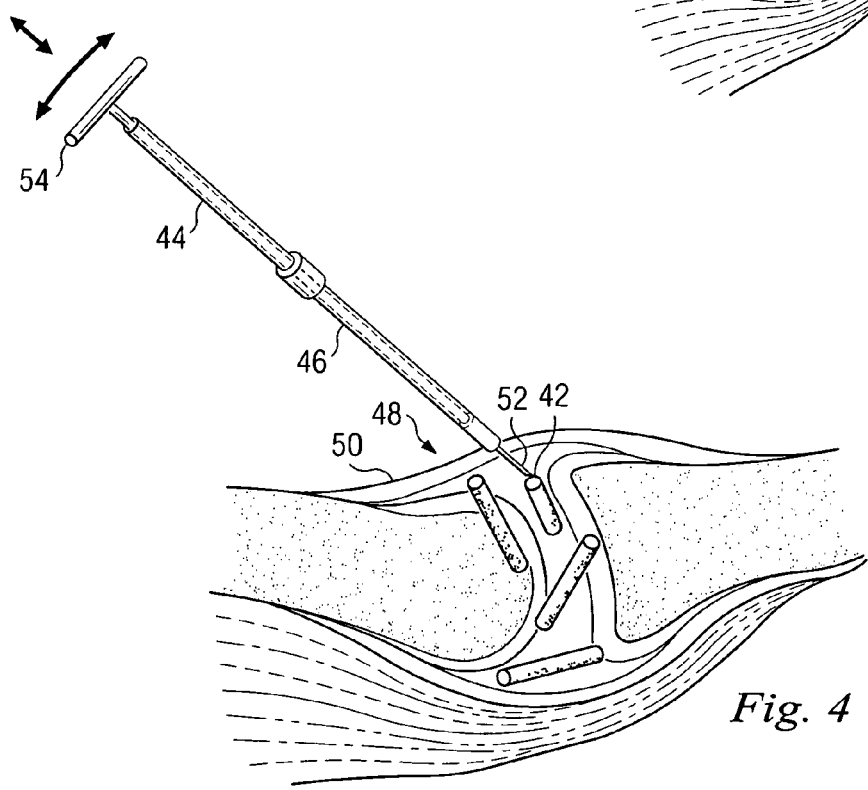

Referring now to FIG. 4, another method for injecting a biological treatment into a facet joint is illustrated. According to the embodiment illustrated in FIG. 4, a biological treatment 42 is provided in the form of microspheres, powders, particulates, pellets, granules, a plug, a solid, porous, woven or non-woven material. Biological treatment 42 may be compressed into a size suitable for delivery through a cannula 44 by pressure and/or heat and/or insertion through a small diameter tube. The delivery cannula 44 is attached to a dilator 46. The biological treatment 42 is inserted into a facet joint 48 by penetrating the capsule 50 of the facet joint with a guide needle 52. Dilator 46, preferably with delivery cannula 44 already attached, is inserted over guide needle 52. A plunger 54 may be used to push the biological treatment from the cannula into the facet joint. The form of the biological treatment may expand upon exiting the dilator, and may further expand as it hydrates or rehydrates in the facet joint.

Figure 5:
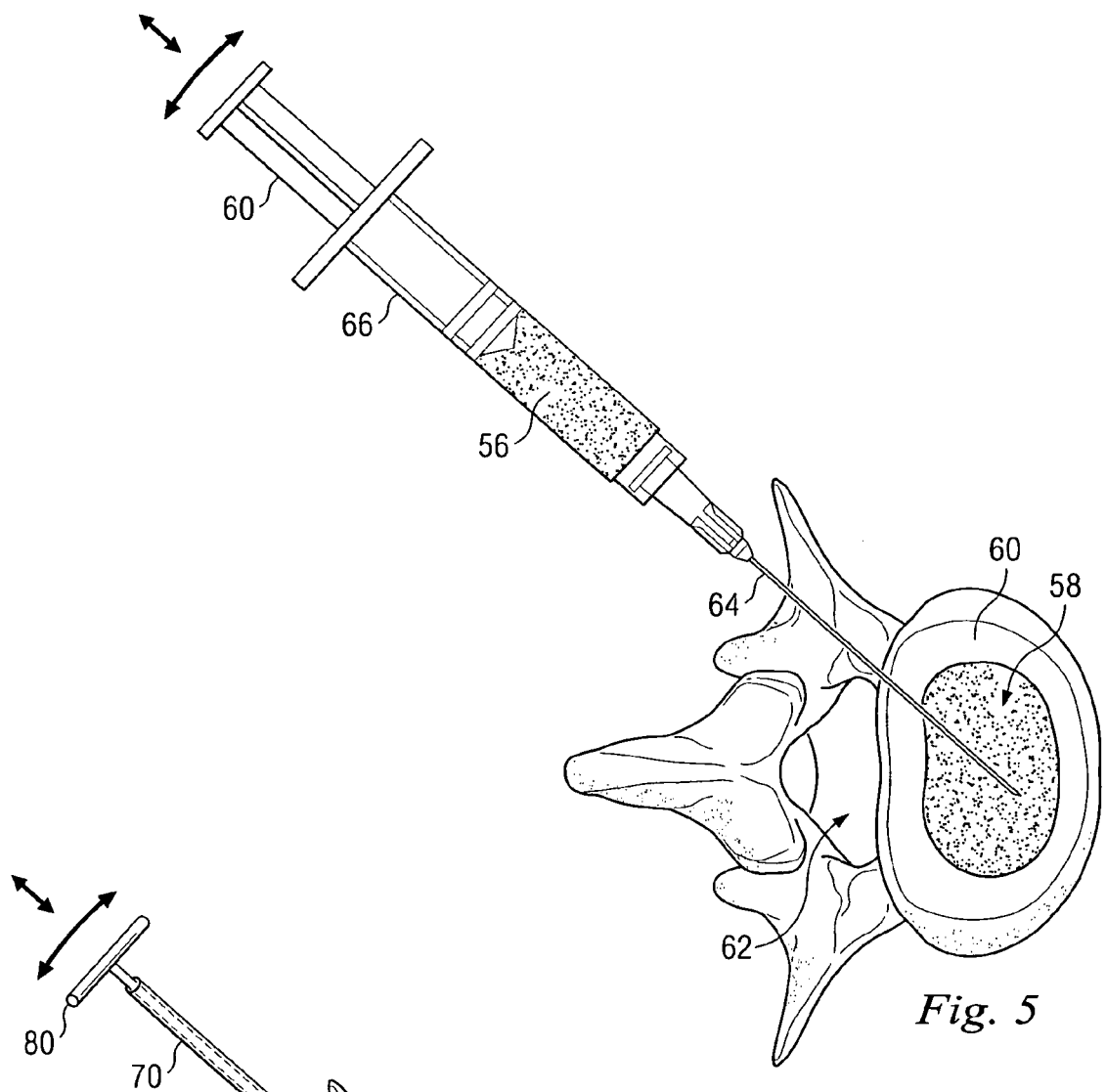
FIGS. 5-6 illustrate methods for applying a biological treatment to a disc space in a vertebral column.

Referring now to FIG. 5, a method for injecting a biological treatment into a disc space is illustrated. According to the embodiment illustrated in FIG. 5, a biological treatment 56 may be injected into the nucleus pulposus 58 contained within a disc annulus 60 in an intervertebral disc space 62. Biological treatment 56 is injected through a hypodermic needle 64 attached to a syringe 66. The syringe 66 is inserted into the nucleus pulposus, and the syringe plunger 68 is depressed, thereby releasing the biological treatment into the disc space 62. As illustrated by the arrows in FIG. 5, the needle/syringe assembly may be moved around, sweeping from side to side and back and forth, to ensure uniform distribution of the biological treatment within the disc space. It is preferred, however, that the tip of the needle be maintained near the center of the disc space to ensure deposition of the material within the nucleus of the disc, and to minimize potential leakage.

Figure 6:
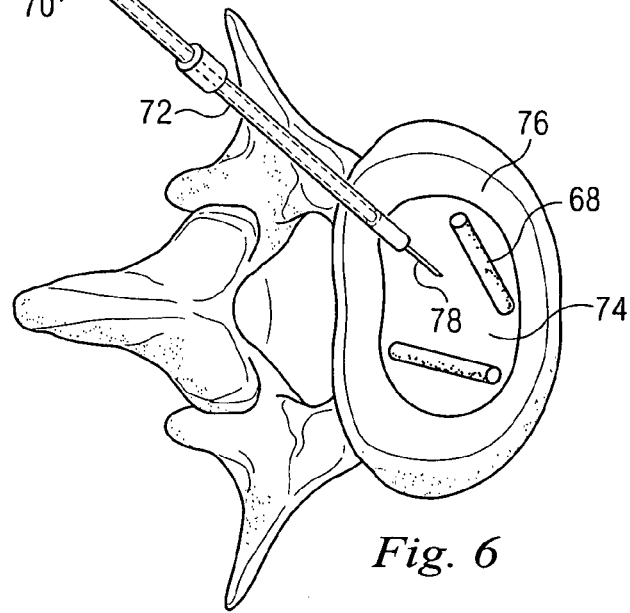

Referring now to FIG. 6, another method for injecting a biological treatment into a disc space is illustrated. According to the embodiment illustrated in FIG. 6, a biological treatment 68 is provided in the form of granules, a plug, a solid, porous, woven or non-woven material. Biological treatment 68 may be compressed into a size suitable for delivery through a cannula 70 by pressure and/or heat and/or insertion through a small diameter tube. The delivery cannula 70 is attached to a dilator 72. The biological treatment 68 is inserted into the nucleus pulposus 74 by penetrating the annulus 76 of the disc with a guide needle 78. Dilator 72, preferably with delivery cannula 70 already attached, is inserted over guide needle 78. A plunger 80 may be used to push the biological treatment from the cannula into the nucleus pulposus. The form of the biological treatment may expand upon exiting the dilator, and may further expand as it hydrates or rehydrates.

Referring now to FIGS. 7A-7F, a method of injecting a biological treatment into a vertebral body and/or an endplate is illustrated.

Figure 7A:
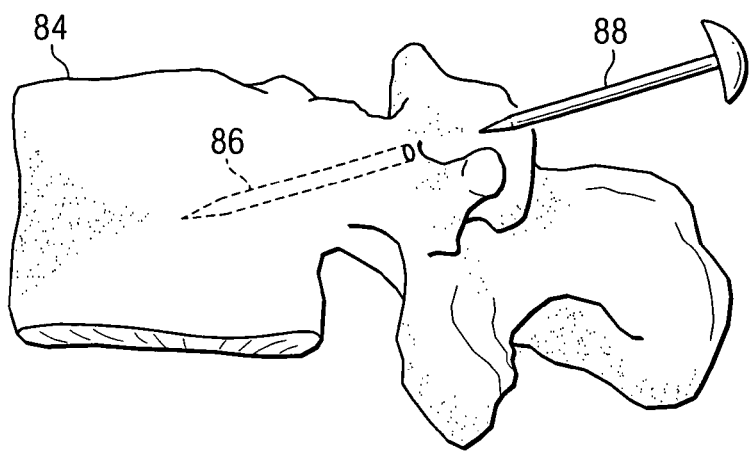
FIGS. 7A-7F illustrate methods for applying a biological treatment to a vertebral body and/or an endplate.
Figure 7B:
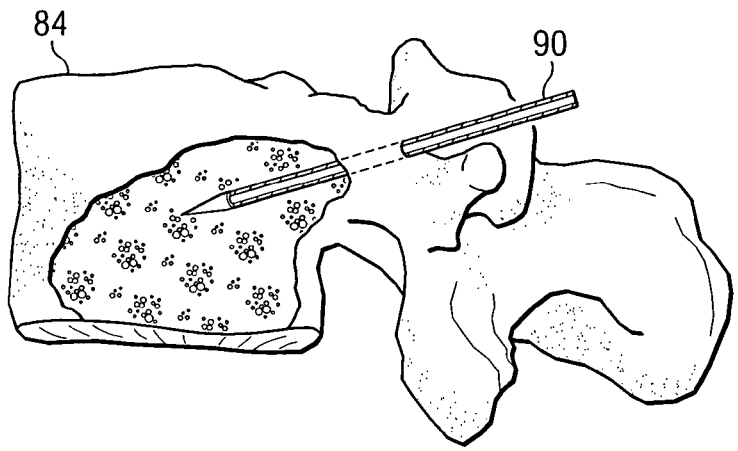
Figure 7C:
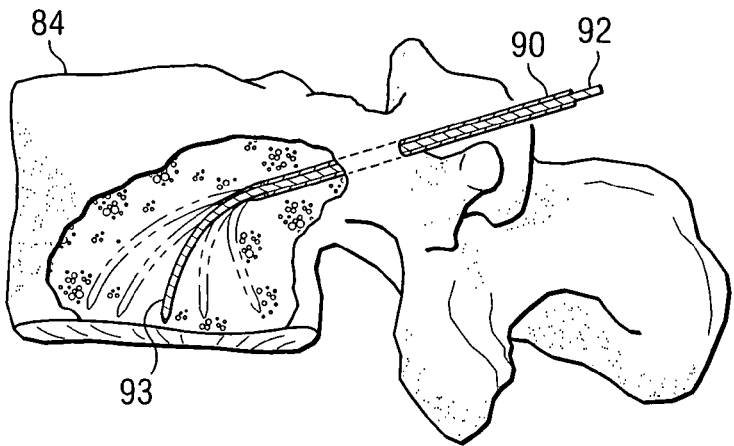

With reference now to FIG. 7A, a channel 86 can be created in vertebral body 84 through the pedicle using a suitable bone-penetrating implement such as a trocar needle 88. A sheath 90 (FIG. 7B) can be inserted into channel 86 through which various procedures can be implemented. FIG. 7C shows a subsequent step in which a flexible or otherwise steerable device 92, such as a needle or drill, is positioned through sheath 90 to access regions nearing the endplate of vertebral body 84. Although FIG. 7C illustrates positioning sheath 90 to access regions near the endplate of vertebral body 84, sheath 90 could also be positioned so as to access regions more central to the vertebral body itself, as opposed to the endplate.

Figure 7D:
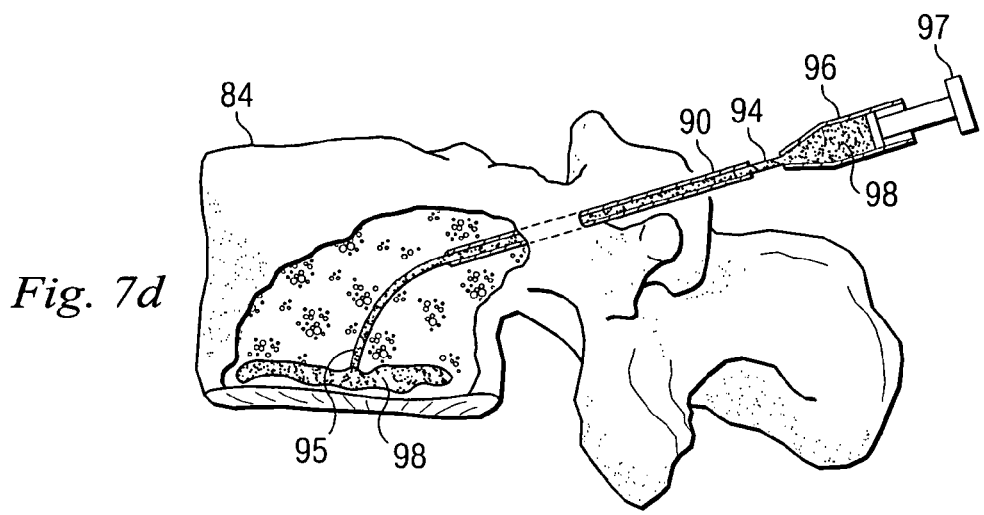
Figure 7E:
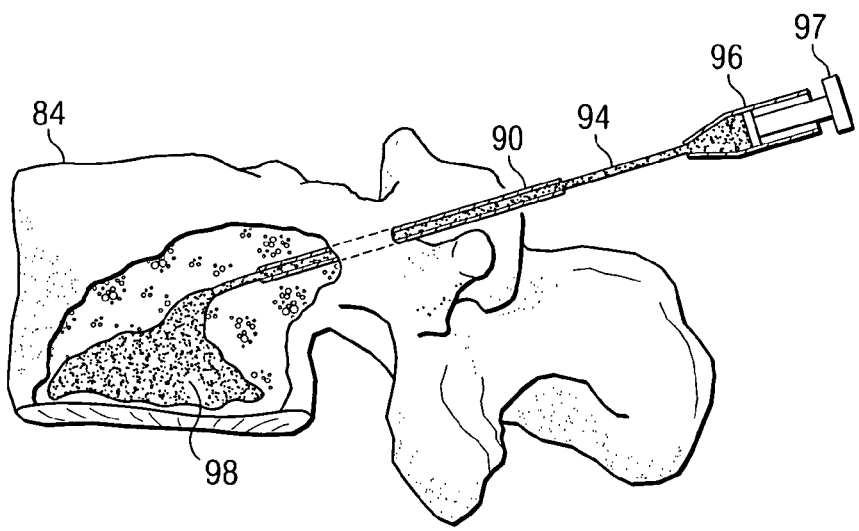
Figure 7F:
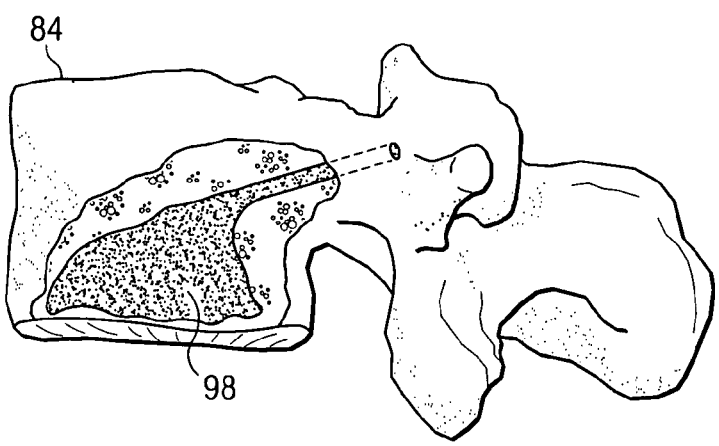

Referring still to FIG. 7C, several directional passes of the steerable device 92 may be used in order to create access to a broader volume of bone. The tip 93 of steerable device 92 can be designed so as to be steerable, for instance by rotation of steerable device 92. As illustrated in FIG. 7D, after accessing near the endplate, (or to the vertebral body itself in other embodiments), the steerable device 92 can be withdrawn, and a delivery device 94 can be inserted through sheath 90. Delivery device 94 can have delivery tip 95, which is curved or otherwise steerable. Delivery device 94 can also include a reservoir 96 and a plunger 97, allowing for the delivery of a biological treatment 98 out of delivery tip 93. FIG. 7E shows an intermediate stage of the delivery process in which additional amounts of the biological treatment 98 are delivered as the sheath 90 and the delivery device 94 are withdrawn from the access channel 86. In this manner, the access channel 86 can be backfilled with the biological treatment 98 as the implements are withdrawn. Finally, shown in FIG. 7F is the biological treatment 98 occupying a volume overlying an endplate of the vertebral body 84, and also backfilled into the access channel 86.

Figure 8A:
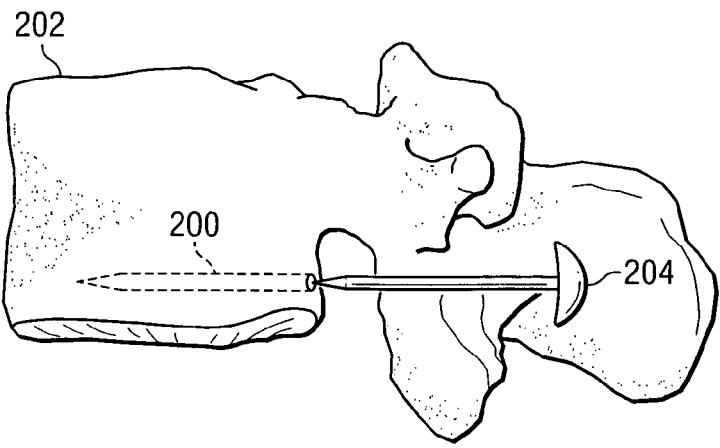
FIGS. 8A-8C illustrate alternative methods for applying a biological treatment to a disc space in a vertebral column.
Figure 8B:
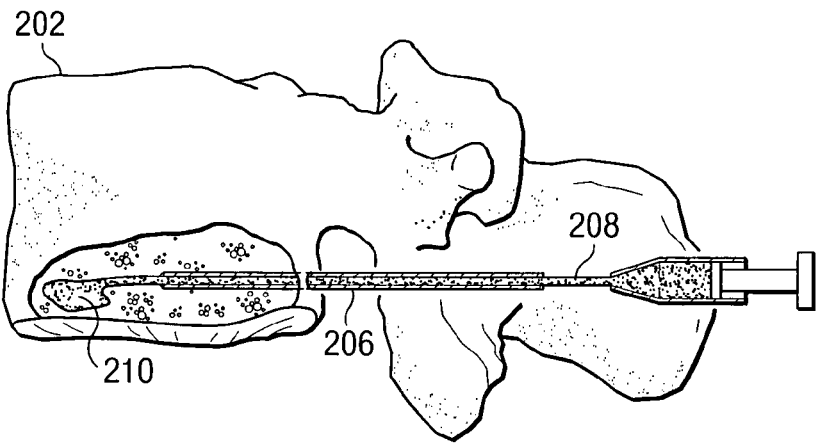
Figure 8C:
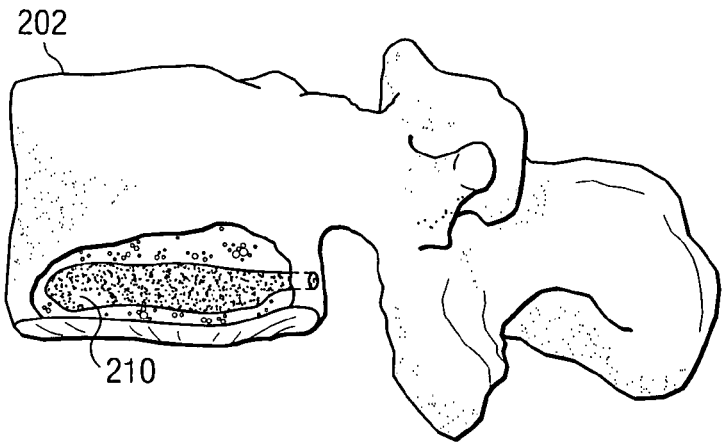

Referring now to FIGS. 8A-8C, another method of injecting a biological treatment into a vertebral body and/or an endplate is illustrated.

With reference now to FIG. 8A, an access channel 200 is created in vertebral body 202 just above the endplate using a bone-penetrating implement 204, for example, a needle. After this access, a sheath 206 is provided into channel 200. A delivery device 208 is then inserted through the lumen of sheath 206 and is used to deliver a biological treatment 210 into the vertebral body in a volume overlying the endplate. If desired or needed, a steerable needle or drill can be used to create access to a broader volume of bone, generally as described in conjunction with FIGS. 7A through 7F above. As well, a backfilling procedure can be used to fill the access channel 200 as the delivery device 208 and sheath 206 are removed. As shown in FIG. 8C, ultimately, a volume of the biological treatment 210 is delivered into the vertebral body overlying the endplate.

In other embodiments, a biological treatment may be introduced into an area of a vertebral column, such as a motion segment, through a needle/trocar assembly, as described in the above-referenced U.S. Patent Application Publication Nos. 2005/0031666. In still other embodiments, a biological treatment may be introduced into an area of a vertebral column by extrusion through a dilated annular opening, infusion through a catheter, insertion through an opening created by trauma or surgical incision, or by other means of invasive or minimally invasive deposition of materials into the area receiving the biological treatment.

According to certain embodiments described herein, when treating a vertebral column with a biological treatment, the load to be imposed on the treated area and/or on surrounding areas is also considered. For example, it can be noted whether the load imposed on a motion segment being treated would adversely affect the success of a biological treatment applied to the motion segment in achieving the desired repair, regeneration, reduction or prevention. By reducing the load imposed on the treated motion segment, the biological treatment is provided an opportunity to perform its function in an area that is less stressed, and therefore more receptive to the intended function of the biological treatment.

Thus, to achieve an improved clinical outcome and a stable result, biological treatments are applied in one or more of the anterior region, anterior column region, posterior region, and spinous process region of a vertebral column, while load-bearing devices and systems for treatment of one or more of the anterior region, anterior column region, posterior region, and spinous process region are also applied to provide a mechanical unloading of the region receiving the biological treatment.

Figure 9:
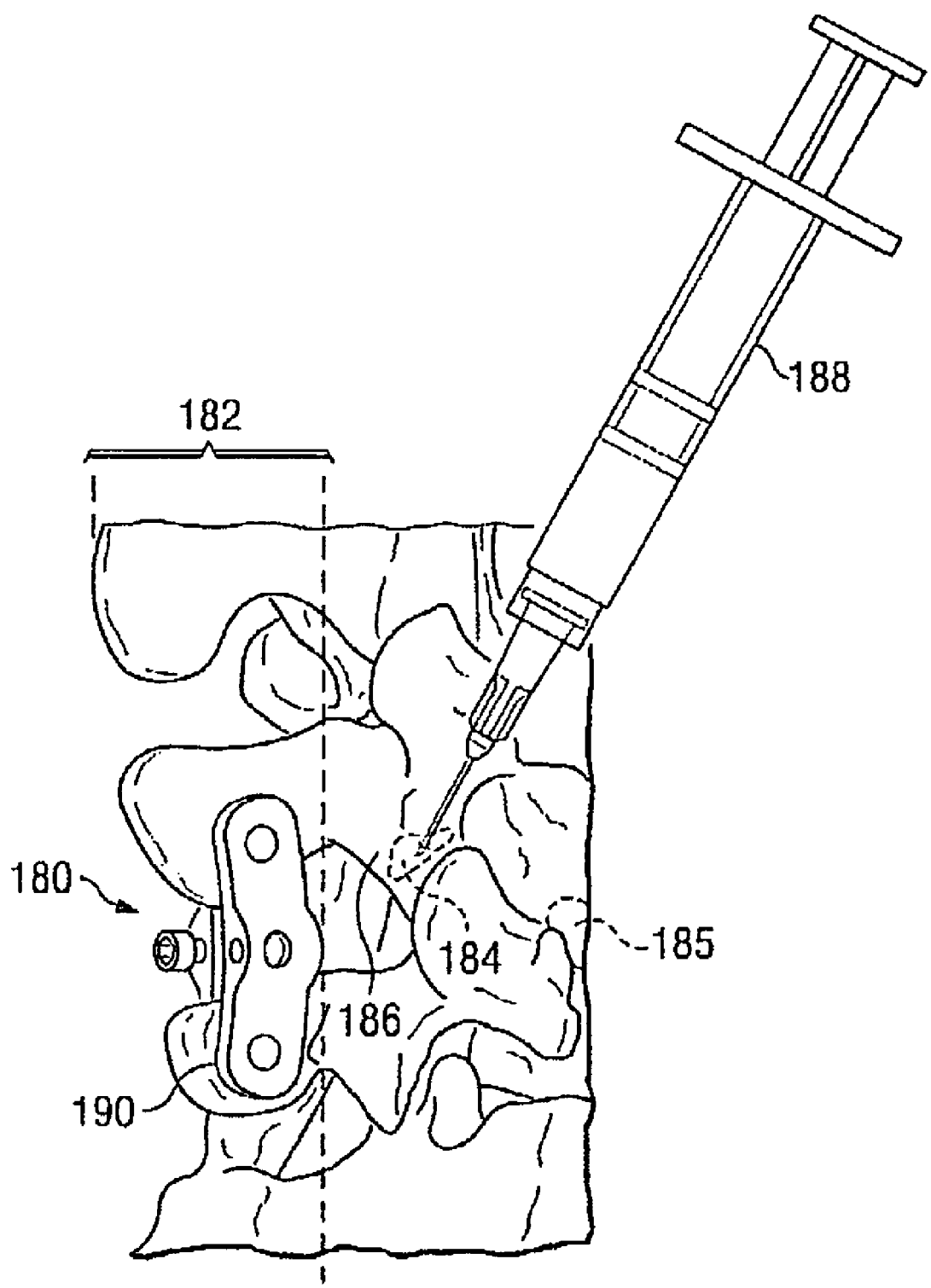
FIG. 9 is a partial posterior view of a vertebral column to which a biological treatment has been applied in combination with a mechanical unloading device.

Biological Treatment of Facet Joint and/or Disc Space Combined with Spinous Process Systems Referring now to FIG. 9, a combined treatment of a vertebral motion segment 180 with a biological treatment and a load-bearing device for treatment of the spinous process region 182 of the spine is illustrated.

A biological treatment 184 has been applied to facet joint 186 by injection with an appropriately sized hypodermic needle 188. Selection of an appropriately sized hypodermic needle for injection into the facet joints of a spine is within the purview of one of ordinary skill in the art. Suitable methods for injecting the biological treatment 184 into the facet joint 186 are described above with respect to FIGS. 3 and 4. Other methods as described herein and as are known to those of ordinary skill in the art may also be used.

In the embodiment illustrated in FIG. 9, a biological treatment 185 has also been applied to disc space, which could include treatment of either or both of the nucleus and the annulus of the disc. Suitable methods for injecting the biological treatment 185 into the disc space are described above with respect to FIGS. 5 and 6. Other methods as described herein and as are known to those of ordinary skill in the art may also be used.

Although two biological treatments 184 and 185 are illustrated, the present disclosure contemplates and includes application of just one biological treatment, or of two or more biological treatments. Moreover, biological treatments can be applied in other areas of the spine, for example, biological treatments can be applied to the anterior longitudinal ligament, the endplates, and the vertebral bodies.

According to the embodiment illustrated in FIG. 9, the treatment of facet joint and the disc space with biological treatments 184 and 185 respectively, is combined with a spinous process device designed for treatment of the spinous process region 182 of the vertebral motion segment 180. The spinous process device is represented in FIG. 9 by spinous process device 190, however the appearance of spinous process device 190 is illustrative only, and it is understood that a wide variety of spinous process devices could be used with the present embodiments.

For example, a spinous process device for treating spinous process region 182 may extend between adjacent spinous processes and/or extend around or through adjacent spinous processes. As one example, spinous process devices may include rigid interspinous process systems such as the Spire Plate system offered by or developed by Medtronic, Inc. of Minneapolis, MN or the X-Stop system offered by or developed by St. Francis Medical Technologies of Alameda, Calif. Such systems may be disclosed in U.S. Published App. No. 2003/0216736 or in U.S. Pat. Nos. 5,836,948; 5,860,977; or 5,876,404, each of which is incorporated by reference herein. Spinous process devices may also include semi-rigid spacer systems having flexible interspinous process sections and flexible ligaments or tethers for attaching around or through spinous processes. Such devices may include the DIAM system offered by or developed by Medtronic, Inc. or the Wallis system offered by or developed by Abbott Laboratories of Abbott Park, IL. Semi-rigid spacer systems may be disclosed in greater detail in U.S. Pat. Nos. 6,626,944 and 6,761,720, each of which is incorporated by reference herein. Alternatively, semi-rigid spacer systems may have rigid interspinous process sections formed of materials such as titanium but incorporating flexible ligament or tethering devices that permit a limited amount of flexion-extension motion at the vertebral joint.

In still another alternative, spinous process devices may include artificial ligaments for connecting two or more spinous processes. In another alternative, spinous process devices may be made of flexible materials such as woven or braided textile based tethers that connect with two or more vertebrae. Elastic or rubber-like materials may also be used in the spinous process region. Suitable spinous process devices may be formed from a variety of materials such as biocompatible metals, polymers, ceramics, and tissue, and combinations thereof. Suitable biocompatible metals include but are not limited to titanium, titanium alloys, nickel titanium, tantalum, stainless steel, and combinations thereof. In some embodiments, the spinous process device may be bioresorbable or partially resorbable.

Any of the foregoing spinous process devices may be combined with any biological treatment. For example, in certain embodiments, a facet joint in a vertebral column receives a biological treatment. In one such embodiment, a biological treatment comprising injectable collagen containing stem cells and TGF-beta 2 is applied to a facet joint in a vertebral column. A spinous process device comprising a semi-rigid spacer system having flexible interspinous process sections and flexible tethers for attaching around or through spinous processes, such as a DIAM system (Medtronic, Inc.) is applied to the spinous process region adjacent to the facet joint receiving the biological treatment to provide a mechanical unloading to the treated facet joint.

In other embodiments, a biological treatment comprising an injectable polyvinyl alcohol hydrogel containing chondrocytes and BMP-7 (OP-1) is applied to a facet joint. A spinous process device comprising a rigid interspinous process system, such as the X-Stop system (St. Francis Medical Technologies) is applied to the spinous process region adjacent to the facet joint receiving the biological treatment to provide a mechanical unloading to the treated facet joint.

In still other embodiments, a biological treatment comprising injectable polyethylene glycol gel containing fibroblasts and TGF-beta 1 is applied to a facet joint. A spinous process device comprising a semi-rigid spacer system having flexible interspinous process sections and flexible tethers for attaching around or through spinous processes, such as a Wallis system (Abbott Laboratories) is applied to the spinous process region adjacent to the facet joint receiving the biological treatment to provide a mechanical unloading to the treated facet joint.

In yet other embodiments, a biological treatment comprising injectable GAG containing chondrocytes and PDGF is applied to a facet joint. A spinous process device comprising a semi-rigid spacer system having flexible interspinous process sections and flexible tethers for attaching around or through spinous processes, such as a DIAM system (Medtronic, Inc.) is applied to the spinous process region adjacent to the facet joint receiving the biological treatment to provide a mechanical unloading to the treated facet joint.

According to still other embodiments, an intervertebral disc space receives a biological treatment. In one such embodiment, a biological treatment comprising injectable allogenic collagen containing stem cells and PDGF is applied to an intervertebral disc. A spinous process device comprising a semi-rigid spacer system having flexible interspinous process sections and flexible tethers for attaching around or through spinous processes, such as a DIAM system (Medtronic, Inc.) is applied to the spinous process region adjacent to the disc receiving the biological treatment to provide a mechanical unloading to the treated disc.

In other embodiments, a biological treatment comprising an injectable polyvinyl alcohol hydrogel containing chondrocytes, TGF-beta 1 and TGF-beta 2 is applied to an intervertebral disc. A spinous process device comprising a rigid interspinous process system, such as the X-Stop system (St. Francis Medical Technologies) is applied to the spinous process region adjacent to the disc space receiving the biological treatment to provide a mechanical unloading to the treated disc.

In still other embodiments, a biological treatment comprising injectable polyethylene glycol gel containing fibroblasts and PDGF is applied to an intervertebral disc. A spinous process device comprising a semi-rigid spacer system having flexible interspinous process sections and flexible tethers for attaching around or through spinous processes, such as a Wallis system (Abbott Laboratories) is applied to the spinous process region adjacent to the disc space receiving the biological treatment to provide a mechanical unloading to the treated disc space.

In yet other embodiments, a biological treatment comprising an injectable porcine-based collagen containing chondrocytes and BMP-12 is applied to a disc space. A spinous process device comprising a semi-rigid spacer system having flexible interspinous process sections and flexible tethers for attaching around or through spinous processes, such as a DIAM system (Medtronic, Inc.) is applied to the spinous process region adjacent to the disc receiving the biological treatment to provide a mechanical unloading to the treated disc.

Depending upon the device chosen, the spinous process device may be installed through open surgical procedures, minimally invasive procedures, injection, or other methods known in the art. The spinous process device may be loaded in compression or tension depending upon the patient's indication or the performance of other implanted systems or biological treatments. For example, a spinous process device 190 may be installed in compression to reduce the load on the facet joint, disc space, or other area where a biological treatment was applied.

According to one embodiment, a procedure for performing the methods described herein includes surgically accessing at least a portion of a patient's spine, and implanting a load-bearing device in the patient's spine. In one aspect, the load-bearing device is implanted so as to mechanically unload all or a portion of the facet joint and/or the disc space, which receives a biological treatment. In another aspect, the load-bearing device is implanted into an area of the spine that is intact, for example, a motion segment where the anatomy has not been surgically disrupted. In yet another aspect, the anatomy of the area of the spine in which the load-bearing device is being implanted has been surgically disrupted, for example, a resection of the facet or the spinous process, or even a discectomy, has been performed.

Whether the spinal anatomy is intact or has been disrupted, the load-bearing device is implanted in to the spine in a position so as to be at least partially load-bearing with respect to the area that is to receive a biological treatment. The device thus mechanically unloads all or a portion of the area to receive the biological treatment. For example, a rigid interspinous process system may be placed on the spinous process region of the spine to transfer load away from the disc space and/or the facets. In one aspect, the facet joints and/or the adjacent vertebral bodies surrounding the disc space are mechanically moved by placement of the mechanical unloading device to align the facet joint and/or increase the distance between the adjacent vertebral bodies. After application of the mechanical unloading device, a biological treatment is applied to at least one facet and/or the disc space. In another aspect, the above-described steps may be reversed such that the biological treatment of the facet joint and/or the disc space occurs first, and the mechanical unloading occurs later.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

For example, each of the following patent applications are incorporated herein by reference, as each describes spinal devices that can be applied to the anterior, anterior column, posterior, or spinous process regions of the vertebral column, and that can be used to unload an area treated with a biological treatment as described herein.

| Title | Ser. No. | Filing Date | Inventor(s) |
|---|---|---|---|
| Materials, Devices, and Methods for Treating Multiple Spinal Regions Including The Interbody Region | 11/331,701 | Jan. 13, 2006 | Hai H. Trieu |
| Materials, Devices, and Methods for Treating Multiple Spinal Regions Including The Posterior and Spinous Process Regions | 11/331,702 | Jan. 13, 2006 | Hai H. Trieu |
| Materials, Devices, and Methods for Treating Multiple Spinal Regions Including The Anterior Region | 11/331,494 | Jan. 13, 2006 | Hai H. Trieu |
| Materials, Devices, and Methods for Treating Multiple Spinal Regions Including Vertebral Body and Endplate Regions | 11/332,013 | Jan. 13, 2006 | Hai H. Trieu |
| Use Of A Posterior Dynamic Stabilization System With An Interdiscal Device | 11/331,924 | Jan. 13, 2006 | Aure Bruneau et al. |

In addition, each of the following applications describes suitable biological treatments that can be applied to an area of the vertebral column, and spinal devices that can be applied to the anterior, anterior column, posterior, or spinous process regions of the vertebral column to unload the treated area. Each of the following applications was filed concurrently with the present application, assigned to the same assignee, and each is hereby incorporated by reference.

| Title | Ser. No. | Filing Date | Inventor(s) |
|---|---|---|---|
| Treatment of the Vertebral Column | 11/354,313 | concurrent with the present application | Hai H. Trieu |
| Treatment of the Vertebral Column | 11/353,517 | concurrent with the present application | Hai H. Trieu |
| Treatment of the Vertebral Column | 11/354,314 | concurrent with the present application | Hai H. Trieu |
| Biological Fusion in the Vertebral Column | 11/354,312 | concurrent with the present application | Hai H. Trieu Mike Sherman |
| Treatment of the Vertebral Column | 11/353,323 | concurrent with the present application | Hai H. Trieu |

It is understood that all spatial references, such as "horizontal," "vertical," "top," "inner," "outer," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method of treating a vertebral column comprising:
    gaining surgical access to a disc space of a vertebral column including introducing a sheath to provide an access path to the disc space;
    resecting at least a portion of the disc space of the vertebral column by introducing a tissue removal device through the sheath to the disc space and moving at least an end portion of the tissue removal device through a removal path to remove the portion of the disc space;
    removing the tissue removal device from the sheath;
    introducing a non-load bearing biological treatment into the resected portion of the disc space of the vertebral column by introducing the non-load bearing biological treatment through a treatment delivery device extending through the sheath and into the disc space and moving at least an end portion of the delivery device through a delivery path while the non-loading bearing biological treatment is emitted from the end portion of the delivery device;
    removing the delivery device and the sheath;
    gaining surgical access to an undamaged, load bearing spinous process region of the vertebral column spaced from the disc space; and
    mechanically unloading the disc space of the vertebral column by applying a load bearing spinal device to at least the spinous process region of the vertebral column.

2. The method of claim 1 wherein the biological treatment comprises a biologically active component.

3. The method of claim 2 wherein the biological treatment further comprises a biological additive.

4. The method of claim 3 wherein the biological additive comprises at least one of a biomaterial carrier, a therapeutic agent, a liquid and a lubricant.

5. The method of claim 3 wherein the biological additive is selected from autogenic collagen, allogenic collagen, xenogenic collagen, human recombinant collagen, gelatin, hyaluronic acid, fibrin, albumin, keratin, silk, elastin, glycosaminoglycans (GAGs), polyethylene glycol (PEG), polyethylene oxide (PEO), polyvinyl alcohol (PVA) hydrogel, polyvinyl pyrrolidone (PVP), co-polymers of PVA and PVP, polysaccharides, platelet gel, peptides, carboxymethyl cellulose, modified starches and celluloses.

6. The method of claim 3 wherein the biological additive is selected from nutrients, analgesics, antibiotics, anti-inflammatories, steroids, antiviricides, vitamins, amino acids and peptides.

7. The method of claim 6 wherein the biological additive comprises at least one of:
    an analgesic selected from codeine, prodrugs, morphine, hydromorphone, propoxyphene, hydrocodone, oxycodone, meperidine, methadone, and fentanyl; and
    an antibiotic selected from erythromycin, bacitracin, neomycin, penicillin, polymyxin B, tetracyclines, viomycin, chloromycetin, streptomycins, cefazolin, ampicillin, azactam, tobramycin, clindamycin and gentamycin.

8. The method of claim 3 wherein the biological additive is selected from water, saline, radio-contrast media, hyaluronic acid, a salt of hyaluronic acid, sodium hyaluronate, glucosaminoglycan, dermatan sulfate, heparin sulfate, chondroitin sulfate, keratin sulfate, synovial fluid, a component of synovial fluid, vitronectin and rooster comb hyaluronate.

9. The method of claim 1 wherein the biological treatment comprises a biologically active component selected from anti-cytokines; cytokines; anti-interleukin-1 components (anti-IL-1); anti-TNF alpha; growth factors; LIM mineralization proteins; stem cell material, autogenic chondrocytes; allogenic chondrocytes, autogenic chondrocytes with one of a retroviral viral vector or a plasmid viral vector; allogenic chondrocytes with one of a retroviral viral vector or a plasmid viral vector; and fibroblasts.

10. The method of claim 1 wherein the biological treatment comprises a biologically active component selected from transforming growth factors, bone morphogenetic proteins, fibroblast growth factors, platelet derived growth factor (PDGF), insulin-like growth factor (ILGF); human endothelial cell growth factor (ECGF); epidermal growth factor (EGF); nerve growth factor (NGF); and vascular endothelial growth factor (VEGF).

11. The method of claim 10 wherein the biologically active component comprises at least one of a transforming growth factor selected from TGF-beta 1, TGF-beta 2, and TGF-beta 3, and a bone morphogenetic protein selected from BMP-2, BMP-3, BMP-4, BMP-6, BMP-7, and BMP-9.

12. The method of claim 1 wherein the biological treatment comprises stem cell material selected from dedifferentiated stem cells, undifferentiated stem cells, mesenchymal stem cells, marrow-extracted stem cell material and adipose-derived stem cell material.

13. The method of claim 1 wherein the biological treatment comprises a biologically active component selected from cartilage derived morphogenetic protein (CDMP); cartilage inducing factor (CIP); proteoglycans; hormones; and matrix metalloproteinases (MMP) inhibitors.

14. The method of claim 1 wherein the biological treatment comprises a biologically active component selected from allogenic disc annulus material, xenogenic disc annulus material, biologic tissues, activated tissue grafts, engineered cells comprising a nucleic acid for encoding a protein or variant thereof, and a recombinant human bone morphogenetic protein.

15. The method of claim 1 wherein:
    the biological treatment comprises allogenic collagen, stem cells and PDGF; and the load-bearing device is applied to the spinous process region adjacent to the disc space receiving the biological treatment.

16. The method of claim 1 wherein:

the biological treatment comprises a polyvinyl alcohol hydrogel, chondrocytes, TGF-beta 1 and TGF-beta 2; and the load-bearing device is applied to the spinous process region adjacent to the disc space receiving the biological treatment.

17. The method of claim 1 wherein:

the biological treatment comprises a polyethylene glycoal gel, fibroblasts and PDGF; and the load-bearing device is applied to the spinous process region adjacent to the disc space receiving the biological treatment.

18. The method of claim 1 wherein:

the biological treatment comprises a porcine-based collagen, chondrocytes, and BMP-12; and the load-bearing device is applied to the spinous process region adjacent to the disc space receiving the biological treatment.

19. The method of claim 1 wherein the load-bearing device is bioresorbable or partially resorbable.

20. The method of claim 1, wherein the tissue removal device comprises a needle.

21. The method of claim 1, wherein the sheath comprises a dilator.

22. The method of claim 1, further comprising inserting the sheath over a guide needle.

23. The method of claim 1, wherein introducing the sheath comprises inserting the sheath over a guide needle.

24. The method of claim 23, wherein the guide needle is a steerable guide needle and wherein the steerable guide needle comprises at least the end portion of the delivery device.

\* \* \* \* \*